(12) United States Patent
Tromberg et al.

(10) Patent No.: US 7,428,434 B2
(45) Date of Patent: Sep. 23, 2008

(54) QUANTITATIVE BROADBAND ABSORPTION AND SCATTERING SPECTROSCOPY IN TURBID MEDIA BY COMBINED FREQUENCY-DOMAIN AND STEADY STATE METHODOLOGIES

(75) Inventors: Bruce J. Tromberg, Irvine, CA (US); Andrew J. Berger, Rochester, NY (US); Albert E. Cerussi, Lake Forest, CA (US); Frederic Bevilacqua, Costa Mesa, CA (US); Dorota Jakubowski, Irvine, CA (US)

(73) Assignee: The Regents of the Univeristy of California, Oakland, CA (US)

( * ) Notice: Subject to any disclaimer, the term of this patent is extended or adjusted under 35 U.S.C. 154(b) by 998 days.

(21) Appl. No.: 10/191,693

(22) Filed: Jul. 9, 2002

(65) Prior Publication Data

US 2003/0023172 A1    Jan. 30, 2003

(51) Int. Cl.
*A61B 6/00* (2006.01)
(52) U.S. Cl. ............... 600/476; 356/300; 356/303; 356/317; 356/318; 356/326; 356/337; 600/473; 600/407; 600/310; 600/322
(58) Field of Classification Search ............... 600/473, 600/476, 407, 310, 322; 356/300, 303, 318, 356/317, 326, 337
See application file for complete search history.

(56) References Cited

U.S. PATENT DOCUMENTS

| 5,371,368 | A   |   | 12/1994 | Alfano et al. |
|---|---|---|---|---|
| 5,424,843 | A   | * | 6/1995  | Tromberg et al. ........... 356/442 |
| 5,441,054 | A   | * | 8/1995  | Tsuchiya ................... 600/310 |
| 5,604,531 | A   |   | 2/1997  | Iddan et al. |
| 5,644,429 | A   |   | 7/1997  | Alfano et al. |
| 5,676,142 | A   | * | 10/1997 | Miwa et al. ................. 600/310 |
| 5,855,205 | A   | * | 1/1999  | Papaionnou ................ 600/407 |
| 5,907,406 | A   | * | 5/1999  | Papaioannou et al. ....... 356/432 |
| 5,999,836 | A   | * | 12/1999 | Nelson et al. ............... 600/407 |
| 6,430,513 | B1  | * | 8/2002  | Wang et al. ................... 702/28 |
| 6,567,678 | B1  | * | 5/2003  | Oosta et al. ................. 600/316 |
| 6,687,532 | B2  | * | 2/2004  | Ohmae et al. ............... 600/425 |
| 6,697,652 | B2  | * | 2/2004  | Georgakoudi et al. ....... 600/310 |
| 6,850,656 | B1  | * | 2/2005  | Bevilacqua et al. ........... 385/12 |

OTHER PUBLICATIONS

Alwin Kienle and Michael S. Patterson Josa A, vol. 14, Issue 1, pp. 246-254—January 1997.☐☐Improved solutions of the steady-state and the time-resolved diffusion equations for reflectance from a semi-infinite turbid medium.*

* cited by examiner

*Primary Examiner*—Brian L. Casler
*Assistant Examiner*—John F Ramirez
(74) *Attorney, Agent, or Firm*—Daniel L. Dawes

(57) ABSTRACT

A technique for measuring broadband near-infrared absorption spectra of turbid media that uses a combination of frequency-domain and steady-state reflectance methods. Most of the wavelength coverage is provided by a white-light steady-state measurement, whereas the frequency-domain data are acquired at a few selected wavelengths. Coefficients of absorption and reduced scattering derived from the frequency-domain data are used to calibrate the intensity of the steady-state measurements and to determine the reduced scattering coefficient at all wavelengths in the spectral window of interest. The absorption coefficient spectrum is determined by comparing the steady-state reflectance values with the predictions of diffusion theory, wavelength by wavelength. Absorption spectra of a turbid phantom and of human breast tissue in vivo, derived with the combined frequency-domain and steady-state technique, agree well with expected reference values.

10 Claims, 9 Drawing Sheets

QUANTITATIVE BROADBAND ABSORPTION AND SCATTERING SPECTROSCOPY IN TURBID MEDIA BY COMBINED FREQUENCY-DOMAIN AND STEADY STATE METHODOLOGIES

GOVERNMENT SUPPORT

The work described herein was supported by the National Institute of Health under grants GM50958 and RR01192 (Laser Microbeam and Medical Program), the U.S. Department of Energy (grant DE-FG03-91ER61227), and the U.S. Office of Naval Research (grant N00014-91-C-0134).

BACKGROUND OF THE INVENTION

1. Field of the Invention

This invention relates to methods and apparatus for analyzing turbid media by means of frequency-domain photon migration measurements and steady-state reflectance measurements. While not limited thereto, this invention is particularly useful for analyzing human body tissue in vivo. As one example, this invention is useful for analyzing female human breast tissue for detecting abnormal tissue conditions.

2. Description of the Prior Art

Reflectance spectroscopy is a technique for characterizing turbid media that has become widely used in medical diagnostics. In many cases quantification of chromophore concentrations is desired, and this requires the ability to separate the effects of absorption from those of scattering. Fundamentally, the coefficient of absorption $m_a$ and the coefficient of reduced scattering $\mu_s'$ can be determined by a series of reflectance measurements performed in one of three domains, namely, time (with a fast pulse of light), frequency (with a sinusoidally modulated source of light), and steady state (with a source of constant intensity but multiple detectors at different distances).

Unsurprisingly, these three techniques have different merits and limitations. Spatially resolved steady-state techniques are relatively inexpensive and are more readily suited for the determination of $\mu_a$ and $\mu_s'$ over large, continuous ranges of wavelengths than are the other methods. However, the steady-state approach works best when measurements are performed with a combination of short (~1 transport mean free path) and long (many transport mean free paths) source-detector separations. Ideally, the optical properties of the sample should not vary over the ranges of volumes probed by the various measurements. The larger the spread of distances probed, the more likely that heterogeneities, such as those found in biological tissue, will distort the data from the predictions of the model. One approach to limiting this effect, given that the shortest separations provide great stability for the calculation of $\mu_s'$, is to use relatively short (<10 mm) source-detector separations. Inasmuch as the mean probing depth scales with the source-detector separation, with this approach such measurements are sensitive to superficial components (to depths of less than 5 mm for typical biological tissues).

Time-domain and frequency-domain techniques are well suited for deeper (>1 cm for biological tissue) investigations. Moreover, they can be performed with only one or a few source-detector separations, which makes them more robust for use in studying heterogeneous samples. Because such techniques require sources that can be pulsed or modulated rapidly, covering a large wavelength range requires a tunable laser or an extensive collection of laser diodes, both of which can be expensive, difficult to maintain, and slow to cover the entire spectrum. This is an important drawback, because the quantification of chromophore concentrations can be significantly affected by use of a limited number of wavelengths.

BRIEF SUMMARY OF THE INVENTION

The present invention provides a way to use steady-state and frequency-domain reflectance measurements in tandem to obtain broad wavelength coverage with increased penetration depth. In accordance with one feature of the invention, there is provided a method of analyzing turbid media. This method comprises performing frequency-domain photon migration measurements on a turbid medium sample. It also includes performing steady-state reflectance measurements on the same turbid medium sample. It further includes combining the results of the frequency-domain photon migration measurements with the results of the steady-state reflectance measurements for obtaining a unique spectrum for the turbid medium sample.

In accordance with another feature of the invention, there is provided a method of analyzing human body tissue in vivo. This method includes emitting light photons from a plurality of different laser diode light sources into human body tissue from a predetermined delivery point on the surface of a human body. This method further includes emitting light photons from a white light source into the same human body tissue from the same predetermined delivery point on the surface of the human body. This method also includes collecting the light photons received at a spaced collection point on the surface of the human body after such light photons have traveled through the human body tissue intermediate the delivery and collection points. This method further includes combining predetermined characteristics of the light photons from the different light sources to provide an indication of the composition of the traversed human body tissue.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

For a better understanding of the present invention, together with other and further advantages and features thereof, reference is made to the following description taken in connection with the accompanying drawings, the scope of the invention being pointed out in the appended claims.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
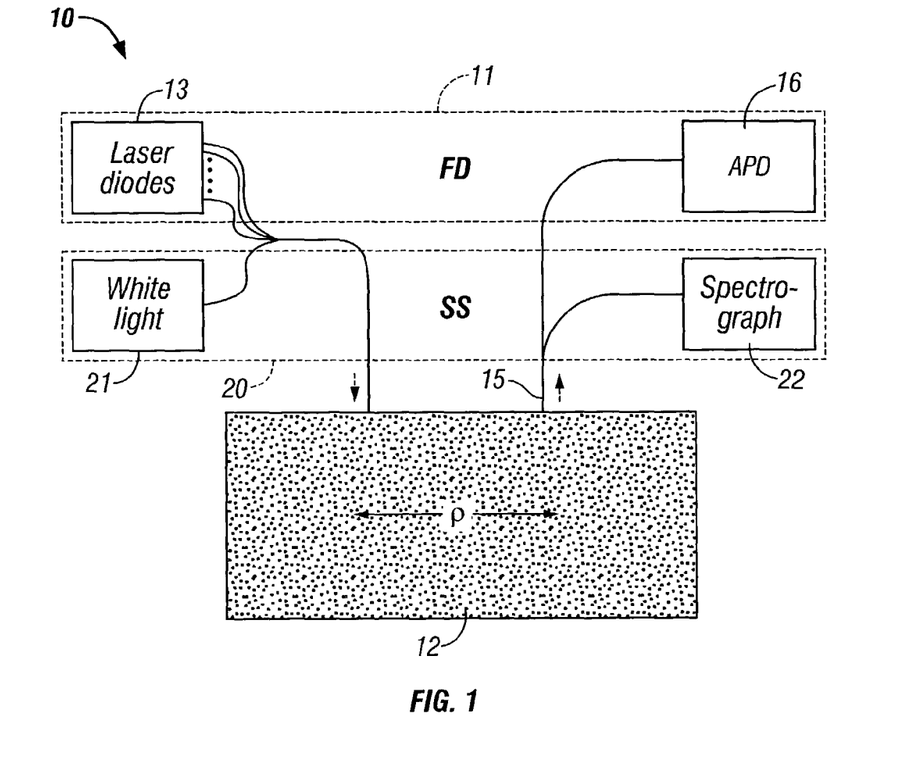
FIG. 1 is a schematic diagram of a representative embodiment of apparatus for practicing the present invention.

Referring to FIG. 1, there is shown a schematic diagram of a representative embodiment of apparatus 10 constructed in accordance with the present invention for analyzing turbid media. Such apparatus 10 includes apparatus 11 for performing frequency-domain photon migration (FDPM) measurements on a turbid medium sample 12. The frequency-domain (FD) apparatus 11 includes a plurality of laser diodes 13 for emitting light energy at a plurality of different wavelengths. In the present embodiment, the plurality of laser diodes 13 includes seven laser diodes which emit light energy at wavelengths of 672, 800, 806, 852, 896, 913 and 978 nanometers (nm). At least one delivery optical fiber 14 is provided for delivering modulated light energy from the laser diodes 13 to a delivery point on the surface of the turbid medium sample 12. The output powers of each of laser diodes 13 is less than 20 milliwatts (mW) at the sample 12.

A mechanism (not shown) is provided for modulating the light energy emitted by the laser diodes 13. This modulating mechanism may take the form described in U.S. Pat. No. 5,424,843, granted on Jun. 13, 1995 to Bruce J. Tromberg et al. This patent describes a form of apparatus for making frequency-domain measurements and the descriptions set forth in this patent are hereby incorporated herein by this reference thereto.

The frequency-domain apparatus 11 further includes a collection optical fiber 15 for collecting emitted light energy from the laser diodes 13 arriving at a collection point on the surface of the turbid medium sample 12 after traveling through the sample 12. The collection point is fixed or located at a predetermined distance "r" from the delivery point. This distance r is, for example, in the range of 15 to 25 millimeters (mm).

The frequency-domain apparatus 11 also includes an analyzer mechanism coupled to the collection optical fiber 15 for measuring at least one characteristic of the modulated light energy received from the laser diodes 13 after passage through the turbid medium sample 12. This mechanism includes an avalanche photodiode (APD) unit 16 that detects the light photons collected by the collection optical fiber 15 and amplifies the alternating-current component of the detected signals. A network analyzer (e.g., a Hewlett-Packard model 8753C) is coupled to the avalanche photodiode unit 16 and measures phase and modulation amplitudes of the detected photon signals.

The analyzing apparatus 10 further includes apparatus 20 for performing steady-state (SS) reflectance measurements on the same turbid medium sample 12. This steady-state apparatus 20 includes a white light source 21 for emitting white light covering the visible spectrum from at least 500 to at least 1200 nm. A suitable white light source is a 150-watt halogen electric lamp. Light energy from the white light source 21 is delivered to the turbid medium sample 12 by way of the delivery optical fiber 14.

The steady-state (SS) apparatus 20 also includes a spectrograph mechanism 22 coupled to the collection optical fiber 15 for receiving white light energy arriving at the collection point on the turbid medium sample 12 and producing therefrom a reflectance spectrum for the sample 12. Spectrograph mechanism 22 may be, for example, an Ocean Optics model S2000 with a linear CCD detector from 525 to 1155 nm. This Ocean Optics spectrograph records a total of 2048 points (0.35 nm/pixel) with a spectral resolution of 5 nm. Relative reflectance is calculated to be the sample value divided by the source value.

When making measurements, the various light sources are operated in a sequential manner. Light energy is emitted by the different laser diodes, one laser diode at a time. Then white light alone is emitted by the white light source for a short time interval. Total measurement time per sample is on the order of 40 seconds (30 seconds for the laser diode measurements and 10 seconds for the white light measurements).

The measured reflectance signal R can be predicted by use of the diffusion approximation to the radiative transfer equation. In this theoretical framework, the reflectance is a function of the optical properties of the medium, defined by the absorption coefficient $\mu_a$, the reduced scattering coefficient $\mu_s'$, and the index of refraction "n". The diffusion approximation is valid for large source-detector separation r $[r>10(\mu_a+\mu_s')^{-1}]$ and high (reduced) albedo $[\mu s'/(\mu_a+\mu_s')>0.95]$. The steady-state and frequency-domain cases can be described by a single formalism in which the solution for the reflectance is built from the Green's function for the diffusion equation, i.e., the fluence (W/cm$^2$) that is due to an isotropic point source in an infinite, homogeneous medium. This function takes the form $\exp(-kr)/(Dr)$, where $D=[3(\mu_a+\mu_s')]^{-1}$, the complex wave number is $k=k_{real}+ik_{imag}$, and $$k_{real} = \left[\frac{3}{2}\mu_a(\mu_a + \mu_a')\right]^{\frac{1}{2}} \left\{\left[1 + \left(\frac{\omega}{\mu_a c}\right)^2\right]^{\frac{1}{2}} + 1\right\}^{\frac{1}{2}}$$

$$k_{imag} = \left[\frac{3}{2}\mu_a(\mu_a + \mu_a')\right]^{\frac{1}{2}} \left\{\left[1 + \left(\frac{\omega}{\mu_a c}\right)^2\right]^{\frac{1}{2}} - 1\right\}^{\frac{1}{2}}$$

where $\omega$ is the modulation frequency in radians per second, and c is the speed of light. The steady-state solution is simply the limit when w=0. In this case, the solution for R is a real number $\{k_{real}=[3\mu_a(\mu_a+\mu_s')]^{1/2}$ and $k_{image}=0\}$. When $\omega>0$, R becomes a complex number $A[\exp(-i\phi)]$, where A is the modulation amplitude and $\phi$ is the phase shift relative to the source. These quantities are obtained from the frequency-domain measurement.

In treating reflectance problems, the sample-air interface is modeled using an extrapolated boundary condition in which the fluence is set to zero at a distance $z_b=2D(1+R_{eff})/(1-R_{eff})$ above the sample $R_{eff}$ depends on the refractive mismatch and equals 0.493 for tissue of n=1.4 and air of n=1.0). The method of images is employed, with an isotropic point source at a depth $z_0=(\mu_a+\mu_s')^{-1}$ contributing a signal $S_r$, and a negative image point at a height $z_0+z_b$ above the extrapolated boundary contributing $S_i$. The result is the fluence $\Phi$ at any point in the sample. The detected signal along the boundary is then written as a combination of terms proportional to the fluence and to its flux normal to the surface:

$$R = c_1\Phi - c_2 D\nabla\Phi \cdot (-\hat{z})$$

where values for the constants $c_1$ and $c_2$ are determined by the refractive index mismatch between the two media (for tissue of n=1.40 and air of n=1, for these constants the values 0.118 and 0.306, respectively, are assumed), $-\hat{z}$ is a unit vector pointing normally upward out of the sample, and $$\Phi = \frac{P}{4\pi D}\left[\frac{\exp(-kr_s)}{r_s} - \frac{\exp(-kr_i)}{r_i}\right]$$

$$D\nabla\Phi\cdot\hat{z} = \frac{P}{4\pi}\left[z_0\left(k+\frac{1}{r_s}\right)\frac{\exp(-kr_s)}{r_s^2} + (z_0+2z_b)\left(k+\frac{1}{r_i}\right)\frac{\exp(-kr_i)}{r_i^2}\right]$$

where P is the incident power and $r_s$ is the distance from the source (image) to the detector.

Each frequency-domain measurement made with each laser diode contains instrumental artifacts. The measured reflectance is actually $$R = C_o A \exp[-i(\phi+\phi_0)] \qquad (3)$$

where $C_o$ and $\phi_0$ are sample-independent instrumental constants. A and $\phi$ are, respectively, the modulation amplitude and phase of the frequency-domain reflectance, as defined above.

For calibration, frequency-domain data is gathered from a prepared sample whose $\mu_a$ and $\mu_s'$ values are known a priori from a set of two-distance frequency-domain measurements. Frequency-dependent values of $\phi_0$ and $C_o$ are calculated from the discrepancies between measured [Equation (3)] and predicted [Equation (1)] phase and modulation amplitude, thus calibrating future measurements.

With the instrumental constants thus determined, the 502 data points per sample (251 for both phase and amplitude as a function of the frequency-domain modulation frequency w) depend on two unknowns, $\mu_a$ and $\mu_s'$. Selection is made of the best $\mu_a$ and $\mu_s'$ values to fit the predictions of Equation (1) to the data, using the iterative, non-linear, least-squares method of Levenberg and Marquardt, simultaneously fitting the phase and the amplitude until overall convergence is achieved. The reflectance in Equation (1) is nearly proportional to either the flux or the fluence term alone (i.e., the ratio of the two is independent of $\mu_a$ and $\mu_s'$) for the large source-detector separations employed in the illustrated embodiment [$>10(\mu_a+\mu_s')^{-1}$]. Consequently, only the fluence term $\Phi$ from Equation (1) is used herein, the additional proportionality factor being absorbed into the instrumental constant $C_o$.

Additional information on the foregoing theory is set forth in a paper by T. H. Pham, O. Coquoz, J. B. Fishkin, E. Anderson and B. J. Tromberg entitled "Broad bandwidth frequency domain instrument for quantitative tissue optical spectroscopy", Rev. Sci. Instrum., vol. 71, pages 2500-2513, (2000). The contents of this paper are hereby incorporated herein by this reference thereto.

Consideration will now be given in regard to how frequency-domain and steady-state measurements can be combined to yield quantitative broadband absorption coefficient ($\mu_a$) spectra. The goal is to compute $\mu_a$ at each wavelength, given the measured steady-state reflectance. However, single-distance steady-state reflectance cannot itself provide $\mu_a$. R depends on $\mu_s'$ as well as on $\mu a$, so one measurement cannot provide a unique determination of either parameter. In addition, the instrumental constant $C_o$ is not known. The single steady-state measurement at each wavelength therefore needs to be supplemented with both a means of establishing the absolute reflectance intensity and an additional piece of information about $\mu_a$ or $\mu_s'$ (or a combination of the two).

The frequency-domain system can provide both pieces of necessary information at each steady-state wavelength over the continuous steady-state spectrum. At first glance, this is surprising because the frequency-domain system operates at only seven discrete wavelengths, whereas the steady-state system covers a 450 nm range with continuous 5-nm resolution. It would seem that the needed values of $\mu_s'$ and $C_o$ could be determined only at those these seven wavelengths, and strictly speaking such is indeed the case. Significantly, however, the wavelength dependence of both $\mu_s'$ and $C_o$ is smooth and predictable in shape. It is this fact that enables use of the discrete frequency-domain information to supplement the broadband steady state measurements at all desired wavelengths.

The frequency-domain measurements permit calculation of the instrumental factor $C_o$ at all wavelengths because no wavelength dependence at all is expected. The sample and source spectra are measured with the same delivery and collection system and only a few seconds apart, so there should be negligible wavelength-dependent artifacts in the ratio of the two. Therefore the task reduces to that of calculating $C_o$ at a single wavelength. This is readily done at any of the frequency-domain wavelengths, as $\mu_a$ and $\mu_s'$ are both known and absolute reflectance is a function only of these variables [cf. Equations (1) and (2) in the $\omega=0$ limit]. Using all the frequency-domain data to increase robustness, we can calculate the value of $C_o$ that scales the measured steady-state reflectances to match the predicted reflectances as closely as possible (in the least-squares sense). Once this is done, the scale factor $C_o$ is known for the entire spectrum.

The frequency-domain values of $\mu_s'$ also allow us to obtain information about $\mu_s'$ across the entire wavelength range. The particle size distribution of scatterers (0.1-10 mm) in many biological media and phantoms tend to have smooth wavelength dependence over the wavelength range 650-1000 nm which is well described by a power function of the form:

$$\mu_s'(\lambda) = A\lambda^{-B} \qquad (4)$$

[the parameter A in Equation (4) is a constant and has no relation to the modulation amplitude]. As a result, measuring several $\mu_s'$ values allows us to fit those values to a simple function of wavelength and to obtain good estimates of $\mu_s'$ at all other wavelengths needed.

Figure 2:
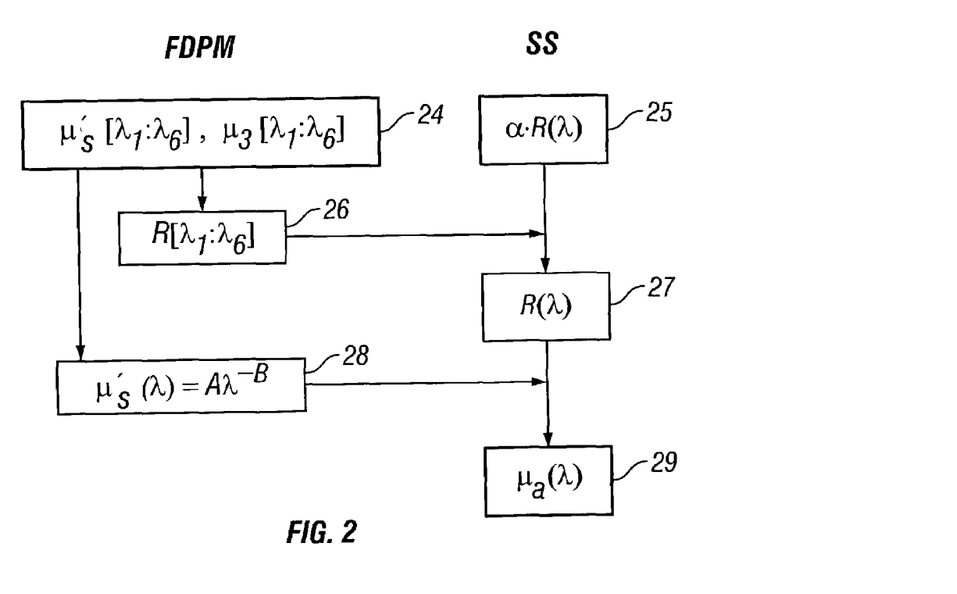
FIG. 2 is a chart used for explaining a representative embodiment of the method of the present invention.

Referring to FIG. 2, there is shown a flowchart for the overall process. As indicated by block 24, the frequency-domain photon migration (FDPM) measurements on the sample provide determinations of the absorption coefficient ($\mu_a$) values and the reduced scattering coefficient ($\mu_s'$) values at the discrete wavelengths $\lambda_1$-$\lambda_6$ of the light energy emitted by the different ones of laser diodes 13. As indicated by block 25, the steady-state (SS) reflectance measurements on the sample provide a determination of a relative reflectance spectrum $\alpha R(\lambda)$ for the sample for the light energy emitted by the white light source 21, where $\alpha$ denotes a proportionality constant. For the present example, the white light energy and, hence, the reflectance spectrum is assumed to cover a wavelength range of 650-1000 nm.

First, the reflectance R predicted by steady-state diffusion theory is calculated at each discrete one of frequency-domain wavelengths $\lambda_1$-$\lambda_6$, using the $\mu_a$ and $\mu_s'$ values supplied by the FDPM measurements 24. This is indicated at block 26. These six reflectance values are absolute reflectance values. By scaling the relative reflectance curve provided by steady-state measurements 25 to fit these six absolute values in a least squares sense, the proportionality factor $\alpha$ is removed and the reflectance spectrum curve is converted to absolute units. This is indicated by block 27, where $R(\lambda)$ denotes the absolute reflectance spectrum.

Next, the scattering coefficient spectrum $\mu_s'(\lambda)$ is deduced from the six $\mu_s'$ frequency-domain measurements. This is indicated by block 28. This is possible because the particle size distribution of scatterers in the samples studied tends to have smooth wavelength dependence over the 600-1000 nm range which is well described by a power function of the form set forth in Equation (4). Consequently, the six measured scattering coefficient values are fitted to the matching power law curve to provide a complete scattering coefficient spectrum curve for the 600-1000 nm range.

As indicated by block 29, the results of the frequency-domain photon migration measurements are combined with the results of the steady-state reflectance measurements to obtain an absorption coefficient spectrum $\mu_a(\lambda)$ for the entire 600-1000 nm range. More particularly, the absorption coefficient spectrum value is numerically calculated at each wavelength from the corresponding calibrated or absolute reflectance value obtained from the calibrated reflectance spectrum curve and the corresponding scattering coefficient value obtained from the scattering coefficient spectrum curve. The $\mu_a(\lambda)$ values were calculated with an in-house Matlab (The Math Works, Inc.) program, making use of the optimization toolbox. Solving for the entire $\mu_a$ spectrum required approximately ten seconds on a personal computer.

The above-described method of combining the steady-state and frequency-domain methods was tested by using it to measure the absorption spectra of turbid samples. Analysis was made of a liquid tissue phantom whose absorption spectrum is known by direct spectrophotometry of the absorbing component before mixing. In vivo measurements were also made on the breasts of two human female volunteers, demonstrating that data can be gathered in vivo and analyzed to provide pertinent physiological parameters.

The phantom contained 17 mg of green dye (naphthol) and 50 mL of an aqueous scattering suspension (Intralipid-20%, Pharmacia, Inc.) dissolved in 950 mL of water. Before the addition of Intralipid, the absorbance spectrum of the dye-water solution was measured in a 1-cm plastic cuvette by a spectrophotometer (Beckman Instruments, DU630) with water as a reference. Optical measurements were performed as indicated in FIG. 1, with the source and detector optical fibers placed at the surface of the sample.

In vivo measurements were performed on the left breasts of two supine female volunteers, aged 37 and 21 years. Data were gathered from two regions on one volunteer (a region on the areolar border and a region close to the middle of the chest) and from one region (inner breast only) on the other volunteer, yielding a total of three samples. The source light was delivered by optical fiber, but the frequency-domain detector was placed directly against the tissue, without a collection fiber. The source fiber and detector were bundled into a single hand-held probe that was placed gently against the breast. The steady-state reflectance was measured subsequently, at the exact same location, in the two-fiber mode shown in FIG. 1.

Figure 3:
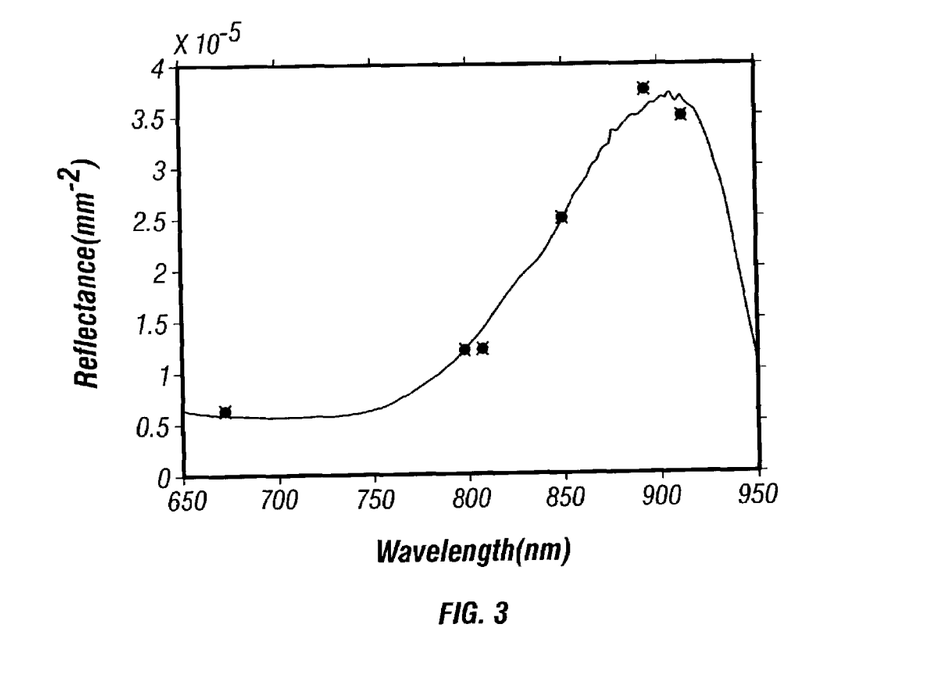
FIG. 3 is a graph of a steady-state reflectance spectrum obtained for a dye-Intralipid phantom.

FIG. 3 is a graph showing the steady-state reflectance measured from the dye-Intralipid phantom (solid curve) and the predicted absolute reflectance calculated from diffusion theory based on the discrete frequency-domain measurements of $\mu_a$ and $\mu_s'$ (solid dots). Because of strong absorption at wavelengths above 950 nm, the frequency-domain measurement at 978 nm was noisy, which in turn made the calculation of steady-state data at wavelengths above 950 nm unstable. Data is therefore presented for 650-950 nm for the phantom only. As anticipated, all the measurements differ from the predictions by essentially the same scale factor. The entire steady-state spectrum is thus converted into absolute reflectance units.

Figure 4:
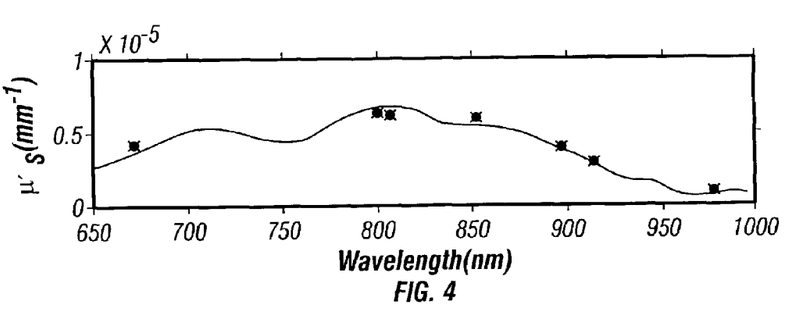
FIGS. 4-6 are graphs of steady-state reflectance spectra acquired from three locations in breast tissue of female volunteers.
Figure 5:
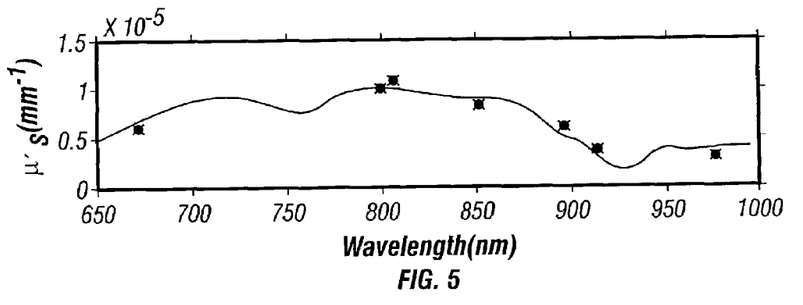
Figure 6:
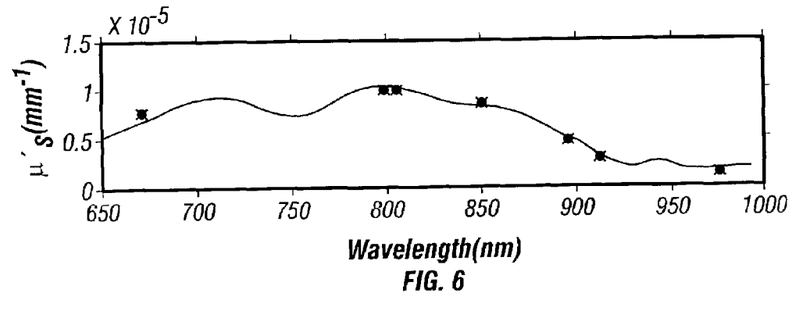

Similar results were obtained for the three female breast samples, as shown in FIGS. 4-6. FIG. 4 is from the inner breast region of the 37-year-old female and FIGS. 5 and 6 are from the areolar border and the inner breast, respectively, of the 21-year-old female.

Figure 7:
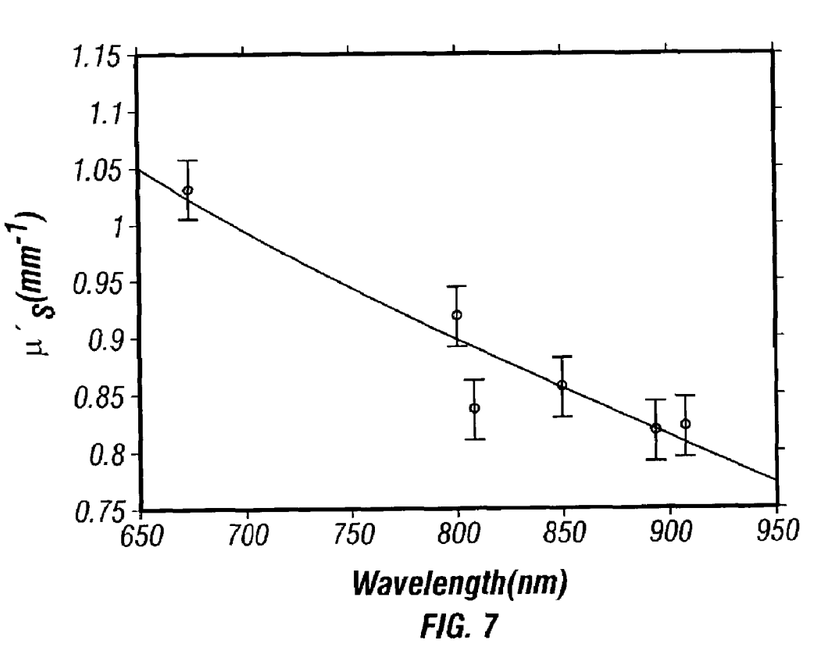
FIG. 7 is a graph of a broadband reduced scattering coefficient spectrum determined for the same dye-Intralipid phantom used for FIG. 3.
Figure 8:
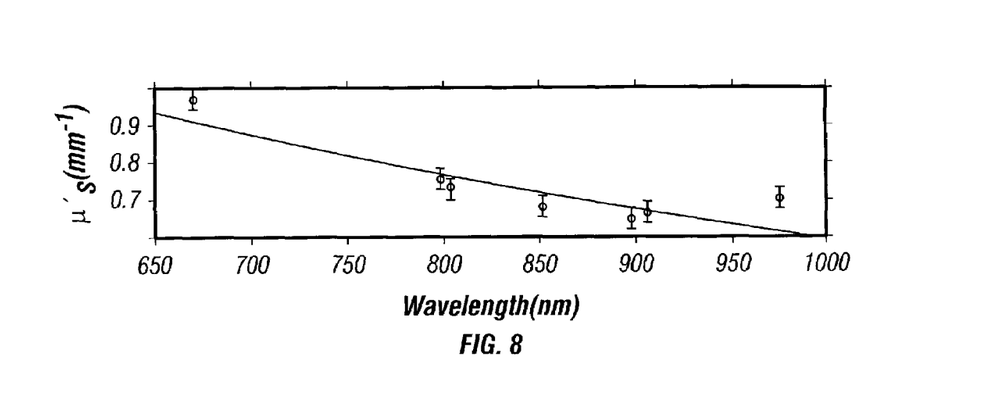
FIGS. 8-10 are graphs of broadband reduced scattering coefficient spectra determined for the three female breast locations of FIGS. 4-6, respectively.
Figure 9:
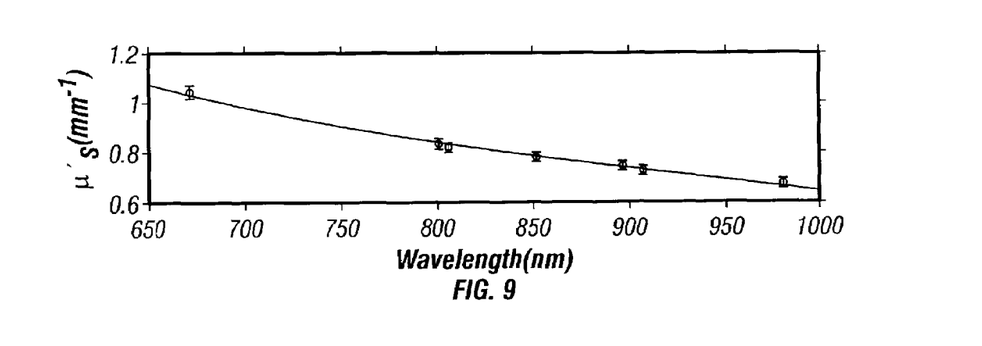
Figure 10:
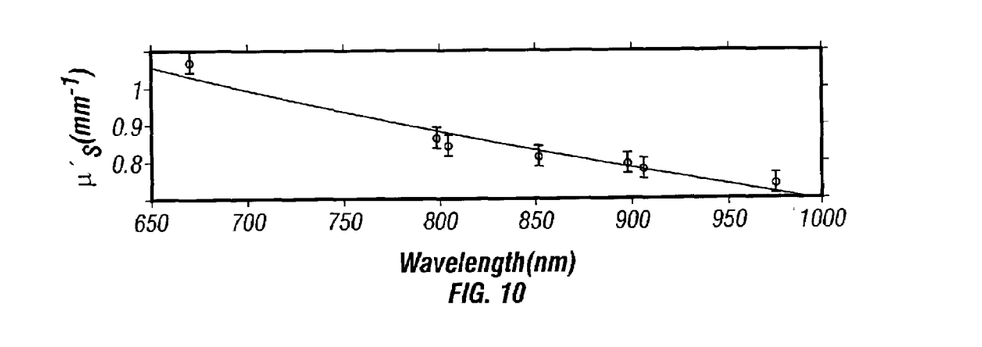

FIG. 7 shows the steady-state scattering coefficient spectrum (solid curve) determined for the dye-Intralipid phantom. Open circles represent the discrete values measured by the frequency-domain technique and the solid curve shows the best power-law fit to Equation (4). Fitting parameters are A=2200 and B=−0.82. Error bars on the discrete values are 3% bars. As expected, the wavelength dependence is fairly smooth and is easily described by the fit. Corresponding fits for the three female breast samples are shown in FIGS. 8-10. Fitting parameters (A,B) are, respectively, (240,−0.86), (2700,−12) and (250,−0.85). Note that the values change by only a factor of two over the entire range, so the wavelength dependence is weak in addition to being predictable.

Figure 11:
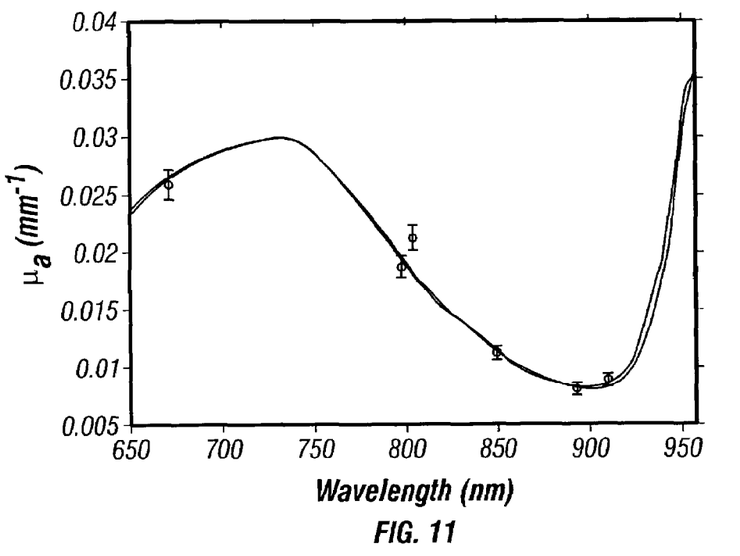
FIG. 11 is a graph of a broadband absorption coefficient spectrum determined for the same dye-Intralipid phantom used for FIG. 3.

FIG. 11 is a graph showing the absorption coefficient ($m_a$) spectrum calculated for the dye-Intralipid phantom. The thicker curve shows the absorption coefficient values that were found to make Equation (1) reproduce the measured reflectance data as closely as possible, using the zero algorithm as described above. The thinner curve represents a linear least-squares fit to the thicker curve based on reference spectra of pure water and pure dye (measured by a spectrophotometer). As FIG. 11 shows, the two-component fit accurately models the measured spectrum across the entire spectral range. Also shown are the values of $\mu_a$ derived by frequency-domain analysis alone (open circles), demonstrating an agreement between the frequency-domain and the combined FD-SS methods at these wavelengths.

Figure 12:
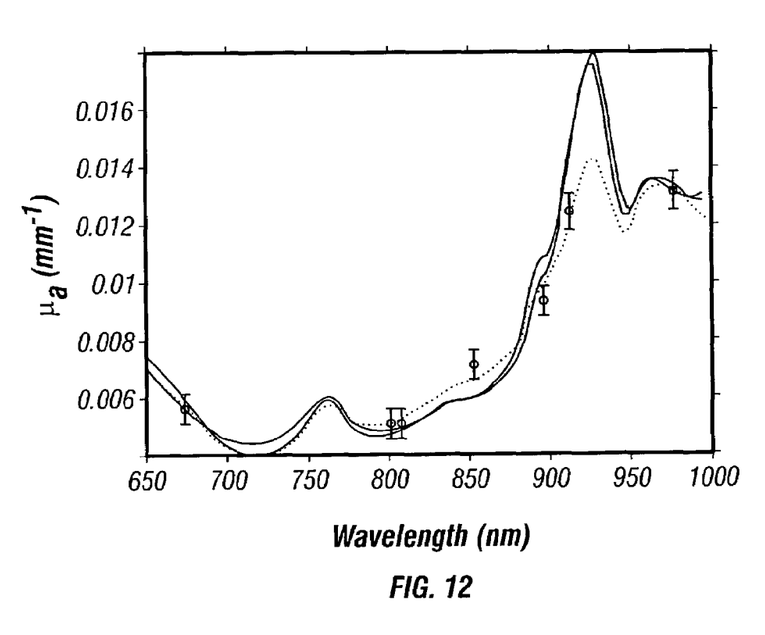
FIGS. 12-14 are graphs of broadband absorption coefficient spectra determined for the three female breast locations of FIGS. 4-6, respectively.
Figure 13:
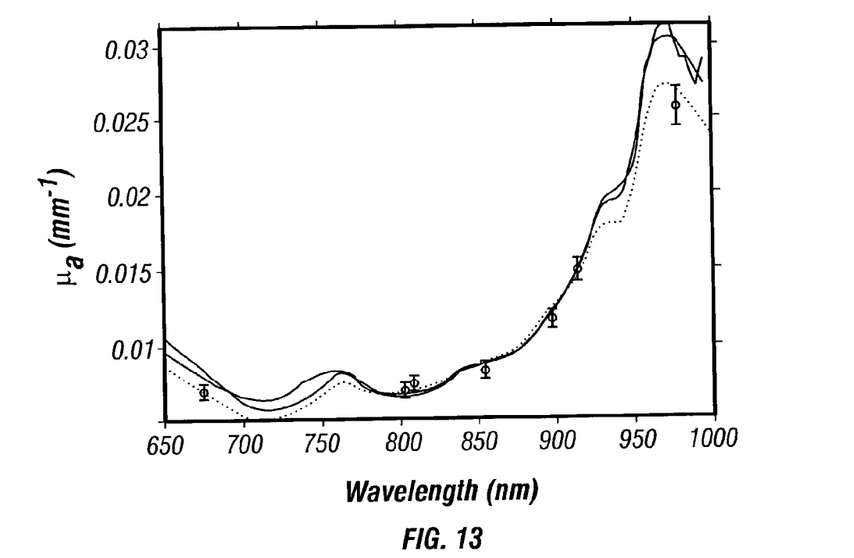
Figure 14:
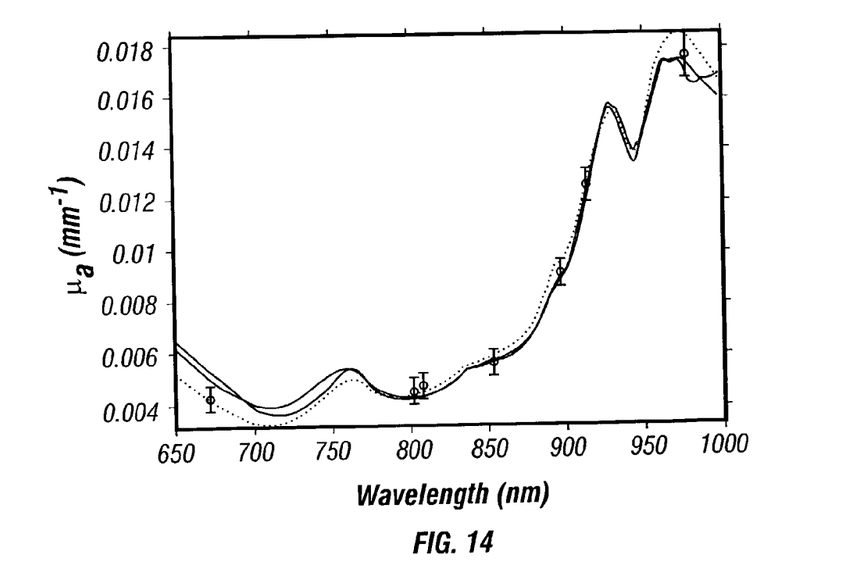

Corresponding plots that show absorption coefficient spectra for the three female breast samples appear in FIGS. 12-14. As before, the thicker curve is the experimental data, the thinner curve is a full spectrum fit and the open circles are frequency-domain values. In these cases, the fit is built from published spectra (FIGS. 15-18) of oxyhemoglobin, deoxyhemoglobin, water and fat, which are commonly regarded as the four major absorbers in breast tissue in the 650-1000 nm range. Coefficients from the fit thus provide estimates of these component concentrations.

For comparison purposes, the dotted curves in FIGS. 12-14 show the spectral fit obtained when only the frequency-domain wavelengths are weighted, as in a customary FD-only experiment. The two spectral reconstructions are clearly different, and these different reconstructions lead to different concentration estimates.

FIG. 12 is for the inner breast measurement on the 37-year-old female. Physiological parameters from this spectral fit are: total hemoglobin concentration, 22 mM; oxygen saturation, 73%; water, 15 g/cm$^3$; fat, 0.75 gm/cm$^3$.

FIG. 13 is for the areolar border breast region of the 21-year-old female. Physiological parameters from FIG. 13 are: total hemoglobin concentration, 30 mM ; oxygen saturation, 70%; water, 0.51 g/cm$^3$; fat, 0.42 g/cm$^3$.

FIG. 14 is for the inner breast of the 21-year-old female. Physiological parameters for FIG. 14 are: total hemoglobin concentration, 19 mM; oxygen saturation, 72%; water, 28 g/cm$^3$; fat, 0.56 g/cm$^3$.

Figure 15:
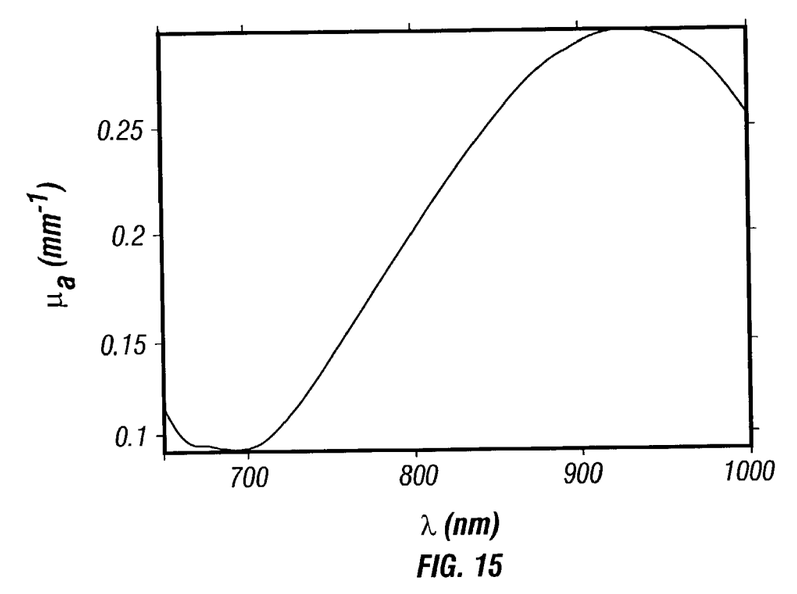
FIGS. 15-18 are graphs of absorption coefficient spectra of major absorbers in breast tissue.
Figure 16:
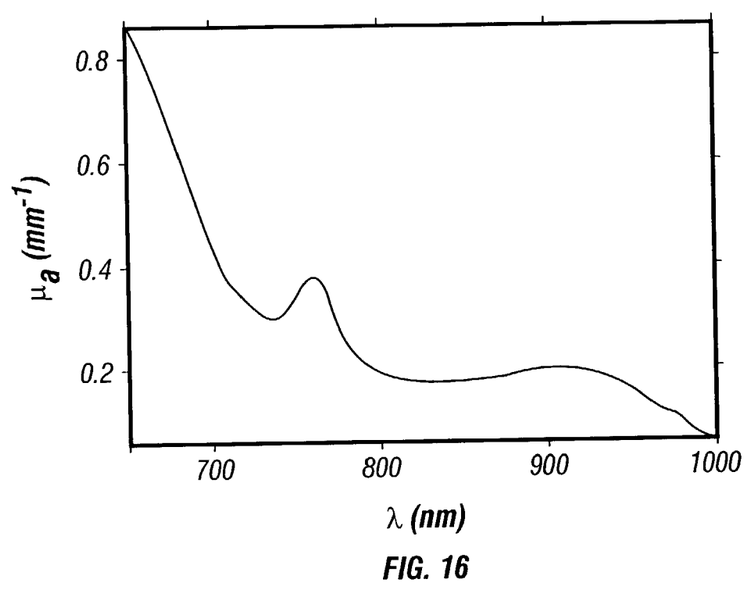
Figure 17:
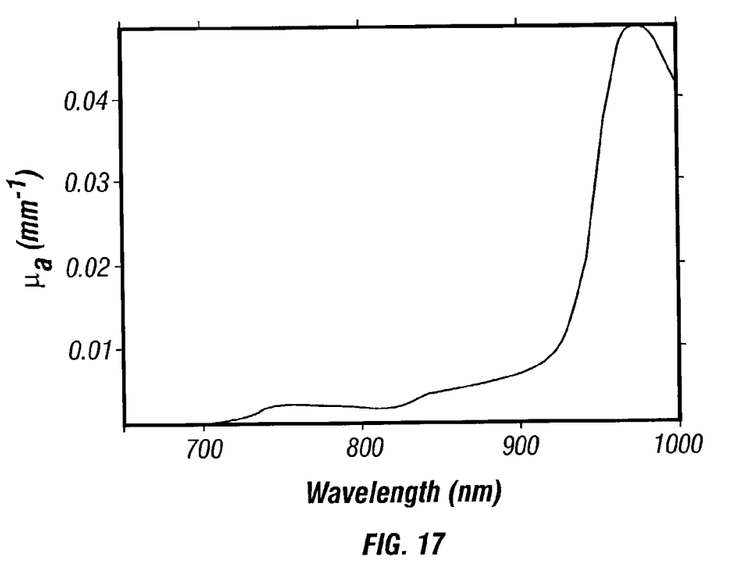
Figure 18:
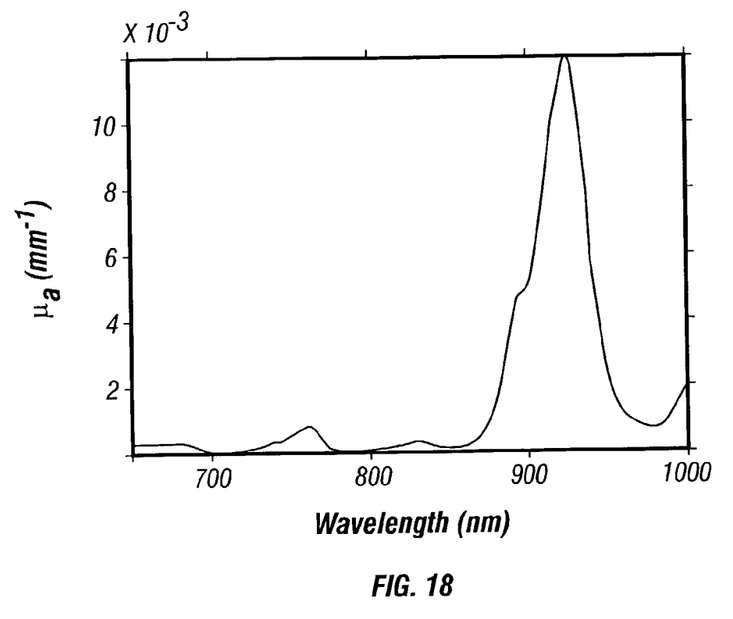

FIGS. 15-18 show the absorption coefficient spectra of major absorbers in breast tissue. FIG. 15 shows the spectrum for oxyhemoglobin, 1 mM. FIG. 16 shows the spectrum for deoxyhemoglobin, 1 mM. FIG. 17 shows the spectrum for water, 1 g/cm$^3$. FIG. 18 shows the spectrum for fat (soybean oil), 0.9 g/cm$^3$.

Compared with discrete wavelength frequency-domain measurements alone, access to a continuous absorption coefficient spectrum offers two important advantages, namely, better chromophore identification and improved concentration quantification. The female breast spectra (FIGS. 12-14) illustrate the usefulness of the combined frequency-domain and steady-state measurements for clinical investigations. Among other things, the resulting indications of tissue composition can be used to detect abnormal tissue conditions.

In summary, the invention can thus be defined as a method of analyzing turbid media comprising the steps of: performing frequency-domain photon migration measurements on a turbid medium sample; performing steady-state reflectance measurements on the same turbid medium sample; and combining the results of the frequency-domain photon migration measurements with the results of the steady-state reflectance measurements for obtaining a unique spectrum for the turbid medium sample.

The unique spectrum is a calibrated reflectance spectrum for the turbid medium sample.

The steady-state reflectance measurements provide a relative reflectance spectrum and the calibrated reflectance spectrum is obtained by scaling the relative reflectance spectrum to fit absolute reflectance values determined at a plurality of discrete wavelengths by the frequency-domain photon migration measurements.

A photon scattering coefficient spectrum is determined from the frequency-domain photon migration measurements, the reflectance measurements provide a reflectance spectrum and the absorption coefficient spectrum is calculated from the scattering coefficient spectrum and the reflectance spectrum.

The frequency-domain photon migration measurements are made at a plurality of discrete wavelengths. The frequency-domain photon migration measurements are made by sequentially exposing the sample to light emitted by a plurality of laser diodes which emit light at different wavelengths. The steady-state reflectance measurements are made by exposing the sample to white light emitted by a white light source.

The invention is also characterized as a method of analyzing turbid media comprising the steps of: performing frequency-domain photon migration measurements on a turbid medium sample at a plurality of discrete wavelengths for determining photon absorption coefficient values and photon scattering coefficient values of the turbid medium at such discrete wavelengths; performing steady-state reflectance measurements on the same turbid medium sample for determining a relative reflectance spectrum for the sample; calibrating the relative reflectance spectrum obtained from the steady-state measurements in accordance with the discrete absorption and scattering coefficient values obtained from the frequency-domain measurements; determining a scattering coefficient spectrum from the discrete scattering coefficient values obtained from the frequency-domain measurements; and combining calibrated reflectance spectrum values and scattering coefficient spectrum values to obtain an absorption coefficient spectrum for the turbid medium sample.

Again the relative reflectance spectrum is calibrated by calculating from the frequency-domain photon migration measurements absolute reflectance values at the discrete wavelengths and scaling the relative reflectance spectrum to fit these absolute reflectance values.

The scattering coefficient spectrum is determined by fitting the scattering coefficient values determined at the discrete wavelengths to a matching power law curve for the desired wavelength range.

The absorption coefficient spectrum is determined by numerical calculation at each wavelength of the absorption coefficient value based on the calibrated reflectance value and the scattering coefficient value obtained from the calibrated reflectance spectrum and scattering coefficient spectrum curves.

The invention can be described as a method of analyzing human body tissue in vivo comprising: emitting light photons from a plurality of different laser diode light sources into human body tissue from a predetermined delivery point on the surface of a human body; emitting light photons from a white light source into the same human body tissue from the same predetermined delivery point on the surface of the human body; collecting the light photons received at a spaced collection point on the surface of the human body after such light photons have traveled through the human body tissue intermediate the delivery and collection points; and combining predetermined characteristics of the collected light photons from the different light sources to provide an indication of the composition of the traversed human body tissue.

The indication of the composition of the traversed human body tissue takes the form of a photon absorption coefficient spectrum for the traversed human body tissue. The light photons from the different light sources are applied in a sequential manner. The human body tissue is female human breast tissue, the delivery and collection points are located on the surface of a female human breast and the resulting indication of tissue composition can be used to detect an abnormal tissue condition.

The invention is still further defined as an apparatus for analyzing turbid media comprising apparatus for performing frequency-domain photon migration measurements on a turbid medium sample; apparatus for performing steady-state reflectance measurements on the same turbid media sample; and apparatus for combining results of the frequency-domain photon migration measurements with results of the steady-state reflectance measurements for producing an absorption coefficient spectrum for the turbid medium sample.

The apparatus for performing frequency-domain photon migration measurements includes: a plurality of laser diodes for emitting light energy at a plurality of different wavelengths; a delivery optical fiber for delivering light energy from the laser diodes to the turbid medium sample; and a mechanism for receiving light energy arriving at a collection point on the turbid medium sample and measuring a characteristic of the collected light energy.

The apparatus for performing steady-state measurements includes: a white light source for emitting white light; a delivery optical fiber for delivering light energy from the white light source to the turbid medium sample; and a spectrograph mechanism for receiving white light energy arriving at a spaced collection point on the turbid medium sample and producing therefrom a reflectance spectrum for the turbid medium sample.

The invention is still further summarized as an apparatus for analyzing turbid media comprising: a plurality of laser diodes for emitting light energy at a plurality of different wavelengths; a mechanism for modulating the light energy emitted by the laser diodes; a white light source for emitting white light; at least one delivery optical fiber for delivering modulated light energy from the laser diodes and white light from the white light source to a delivery point on a surface of a turbid medium sample; a collection optical fiber for collecting emitted light energy arriving at a collection point on the surface of the turbid medium sample after traveling through the turbid medium sample, such collection point being fixed at a predetermined distance from the delivery point; an analyzer mechanism coupled to the collection optical fiber for measuring at least one characteristic of the modulated light energy received from the laser diodes after passage through the turbid medium sample; a spectrograph mechanism coupled to the collection optical fiber for producing a reflectance spectrum for the white light received from the white light source after passage through the turbid medium sample; and a data processing mechanism for combining results of the analyzer mechanism measurements with results of the spectrograph mechanism measurements for producing a photon absorption coefficient spectrum for the turbid medium sample.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of analyzing turbid media comprising:
    performing frequency-domain photon migration measurements on a turbid medium sample at a plurality of specified wavelengths for determining absolute photon absorption coefficient values and absolute photon scattering coefficient values of the turbid medium at such discrete wavelengths;
    performing steady-state measurements on the same turbid medium sample for determining a relative spectrum for the sample;
    calibrating the relative spectrum obtained from the steady-state measurements in accordance with the discrete absorption and scattering coefficient values obtained from the frequency-domain measurements;
    determining a scattering coefficient spectrum from the discrete scattering coefficient values obtained from the frequency-domain measurements; and
    combining calibrated spectrum values and scattering coefficient spectrum values to obtain an absorption coefficient spectrum for the turbid medium sample.

2. A method in accordance with claim 1 wherein the relative spectrum is calibrated by calculating from the frequency-domain photon migration measurements absolute values at the specified wavelengths and scaling the relative spectrum values to fit these absolute reflectance values.

3. A method in accordance with claim 1 wherein the scattering coefficient spectrum is determined by fitting the absolute scattering coefficient values determined at the specified wavelengths to a matching power law curve for the desired wavelength range.

4. A method in accordance with claim 1 wherein the absorption coefficient spectrum is determined by numerical calculation at each wavelength of the absolute absorption coefficient value based on the calibrated reflectance value and the scattering coefficient spectrum obtained from the calibrated reflectance and/or transmittance spectrum and absolute scattering coefficient spectrum curves.

5. A method of analyzing turbid tissue comprising:
    simultaneously emitting light from a plurality of different modulated light sources into tissue;
    emitting light from a steady state broadband or multi-spectral light source into the tissue;
    collecting the light received at a spaced collection point on the surface of the human body after such light have traveled through the human body tissue intermediate the delivery and collection points; and
    combining predetermined characteristics of the collected light from the different modulated light sources used in a frequency-domain photon migration measurement with the light from the steady state broadband or multi-spectral source used in steady-state measurements to provide a light spectrum as an indication of the composition of the traversed human body tissue based on an optical model.

6. A method in accordance with claim 5 wherein the indication of the composition of the traversed human body tissue takes the form of a photon absorption coefficient spectrum for the traversed human body tissue.

7. A method in accordance with claim 5 wherein the light photons from the different light sources are applied in a sequential manner.

8. A method of analyzing turbid media comprising:
performing frequency-domain photon migration measurements on a turbid medium sample within a first spectral range;
performing steady-state measurements within a second spectral range on the same turbid medium sample; and
combining the results of the frequency-domain photon migration measurements with the results of the steady-state measurements for obtaining a unique spectrum for the turbid medium sample across the second spectral range, which is greater than the first spectral range.

9. An apparatus for analyzing turbid media comprising:
means for performing frequency-domain photon migration measurements on a turbid medium sample using a limited number of optical wavelengths;
means for performing broadband steady-state measurements on the same turbid media sample; and
means for combining results of the frequency-domain photon migration measurements with results of the steady-state measurements for producing an absorption coefficient spectrum for the turbid medium sample over a spectral range as defined by the means for performing broadband steady-state measurements.

10. Apparatus for analyzing turbid media comprising:
a plurality of laser diodes for emitting light energy at a plurality of different wavelengths;
means for modulating the light emitted by the laser diodes;
a broadband, steady state light source having a defined spectral range;
where modulated light from the laser diodes and light from the broadband light source is delivered in free space to a delivery point on a surface of a turbid medium sample;
a collection point on the surface of the turbid medium sample for collecting light after propagation through the turbid medium sample, such collection point being fixed at a predetermined distance from the delivery point;
an analyzer for measuring at least one characteristic of the modulated light received in free space at the collection point from the laser diodes after propagation through the turbid medium sample;
a spectrograph for producing a spectrum of the light received in free space at the collection point from the broadband light source after propagation through the turbid medium sample; and
a data processing circuit which combines the results of the analyzer with results of the spectrograph to produce an absorption coefficient spectrum of the turbid medium sample as defined by the spectral range of the broadband light source.

* * * * *